United States Patent [19]
Santori et al.

[11] Patent Number: 5,810,820
[45] Date of Patent: Sep. 22, 1998

[54] ENDOMEDULLAR DEVICE FOR NAILING LONG DISTANCE

[76] Inventors: Francesco Saverio Santori, 9 Via Ronciglione, Rome, Italy, I-00191; Marco Ottieri Tonci, 9 Via E. Manfredi, Rome, Italy, I-00197

[21] Appl. No.: 751,060

[22] Filed: Nov. 15, 1996

[30] Foreign Application Priority Data

May 20, 1994 [IT] Italy .................................. TO95A0407

[51] Int. Cl.$^6$ .................................................. A61B 17/72
[52] U.S. Cl. ............................................. 606/63; 606/64
[58] Field of Search .................................. 606/63, 64, 62, 606/60, 68, 67

[56] References Cited

U.S. PATENT DOCUMENTS

| | | | |
|---|---|---|---|
| 3,760,802 | 9/1973 | Fischer et al. | 606/63 |
| 4,227,518 | 10/1980 | Aginsky | 606/63 |
| 5,057,103 | 10/1991 | Davis | 606/63 |
| 5,116,335 | 5/1992 | Hannon et al. | 606/62 |
| 5,281,225 | 1/1994 | Vicenzi | 606/62 |
| 5,562,665 | 10/1996 | Young | 606/62 |

FOREIGN PATENT DOCUMENTS

| | | | |
|---|---|---|---|
| 31834 | 4/1969 | Germany | 606/68 |
| 1338853 | 9/1987 | U.S.S.R. | 606/68 |

*Primary Examiner*—Guy V. Tucker
*Attorney, Agent, or Firm*—Paul J. Cook

[57] ABSTRACT

An endomedullar device for nailing long bones is disclosed. The device includes an elongated tubular body for insertion inside the bone. A connecting mechanism for connecting the body to the bone is made up of at least a pair of deformable nails and an operating mechanism for moving the deformable nails between a withdrawn idle position inside the tubular body and an operating position where the nails project outward of the tubular body and into the bone.

17 Claims, 5 Drawing Sheets

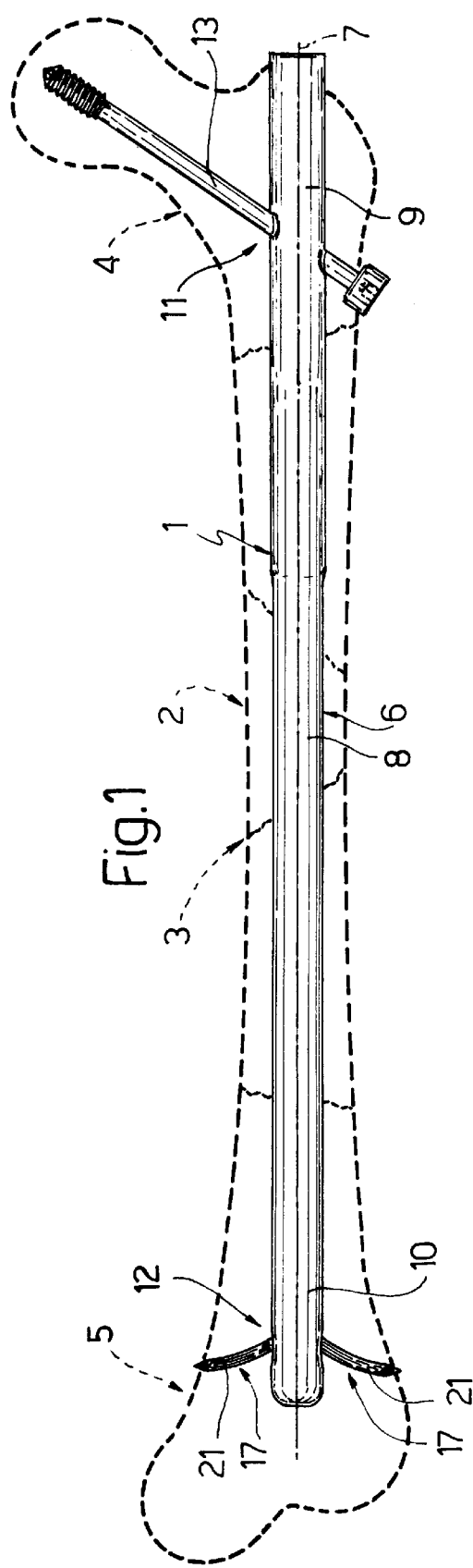
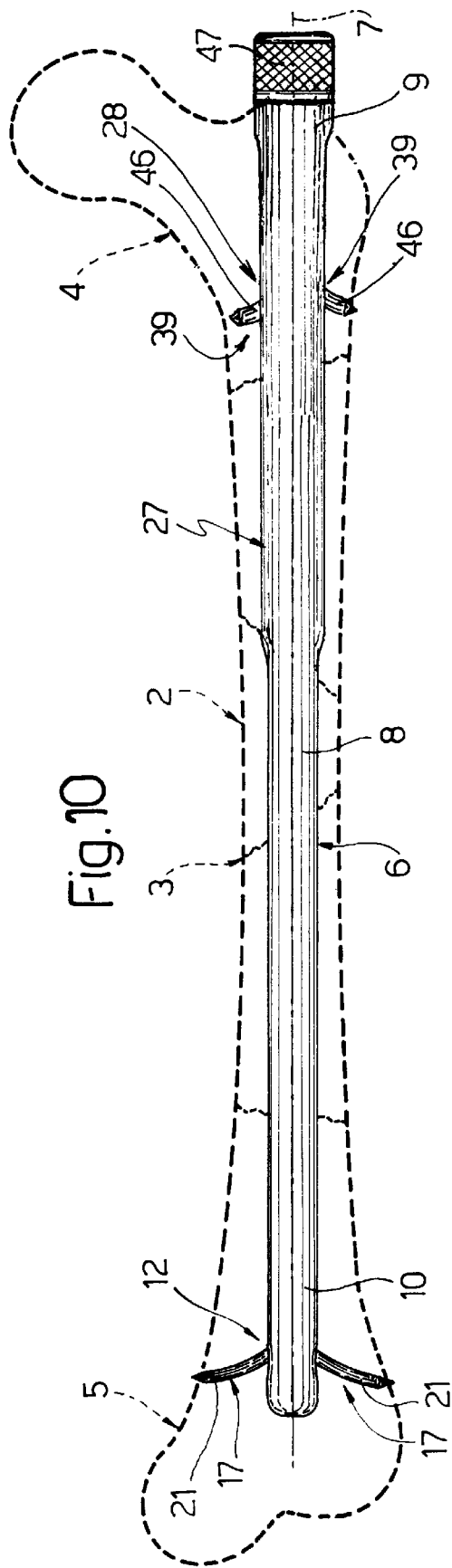

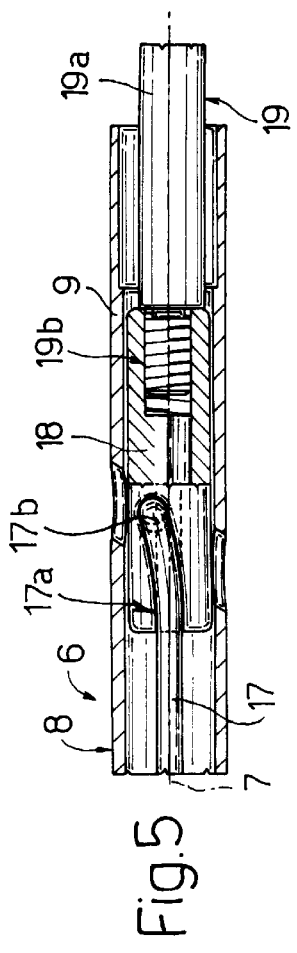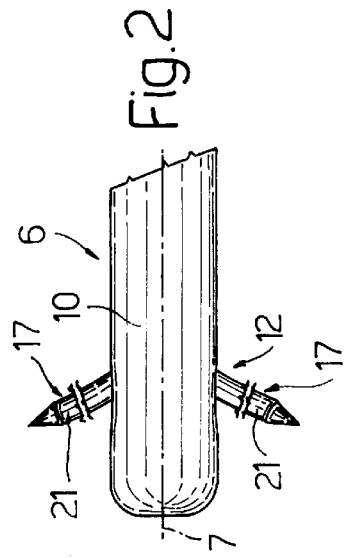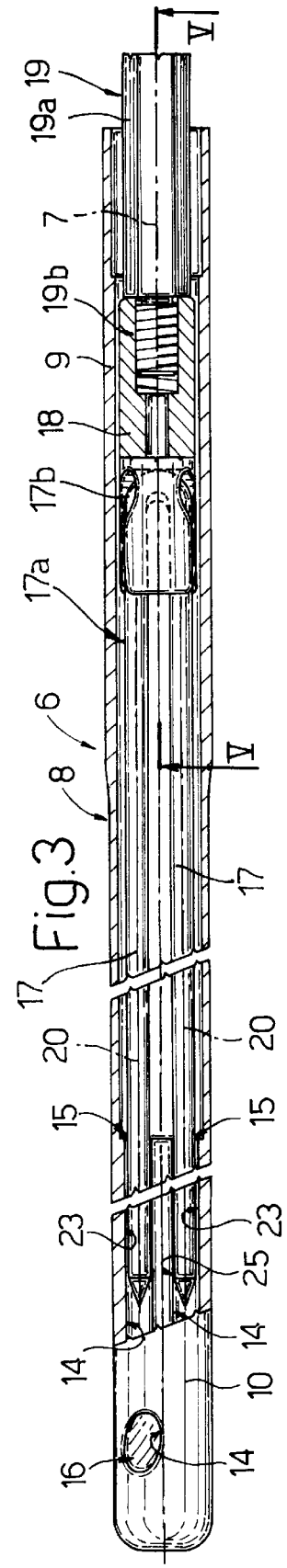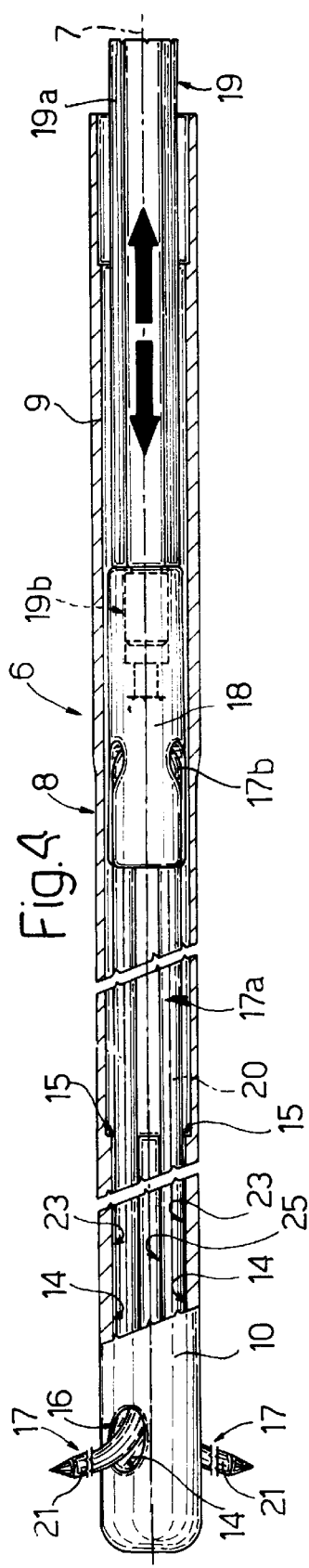

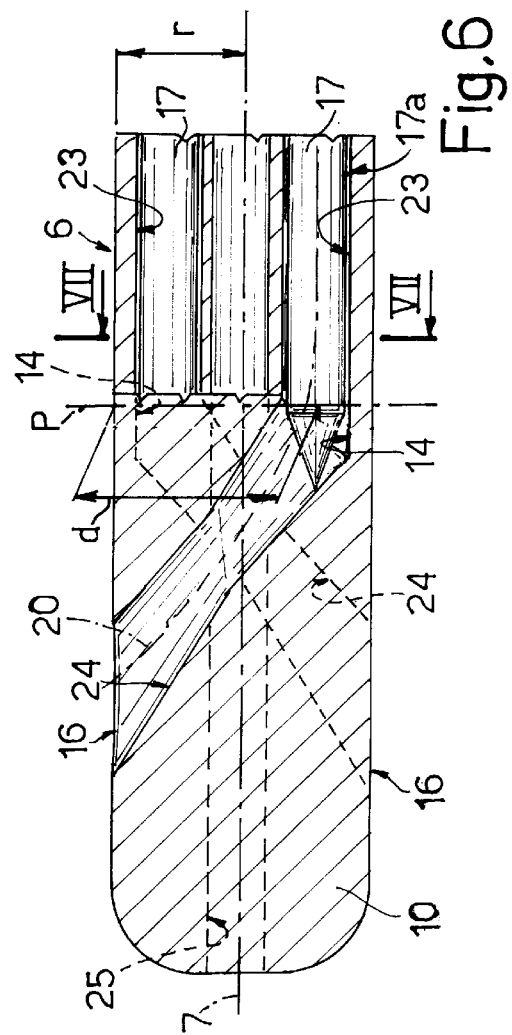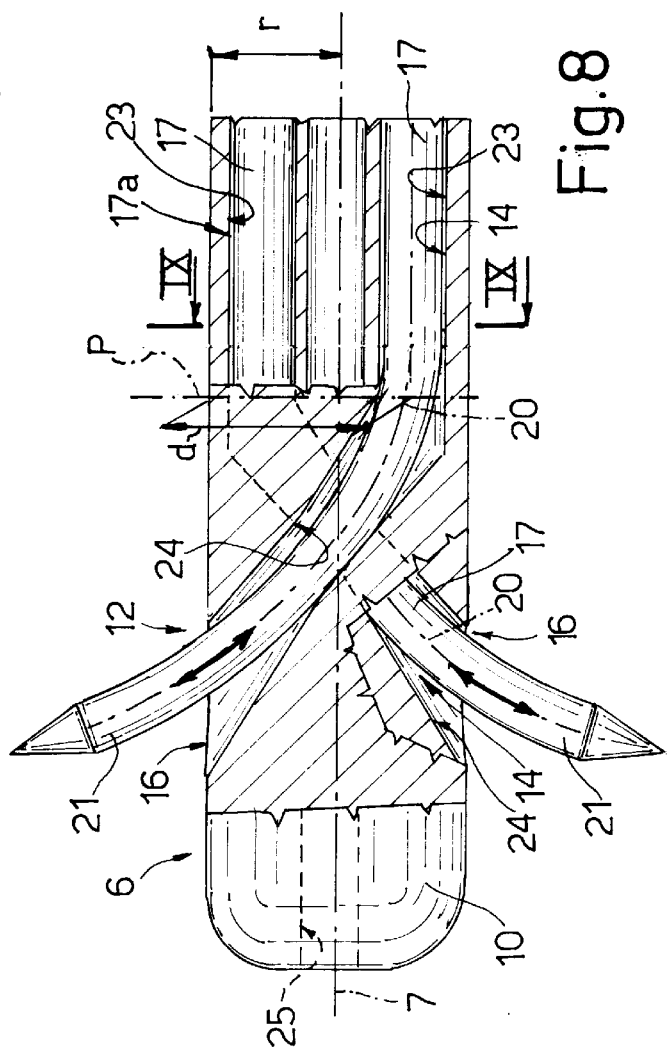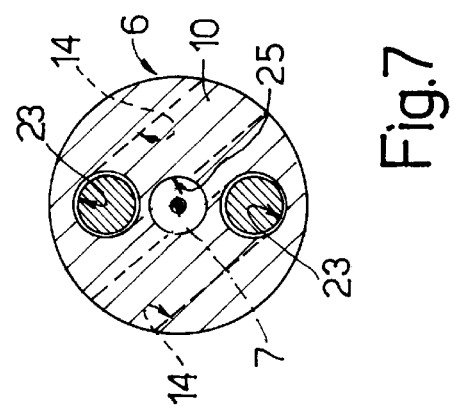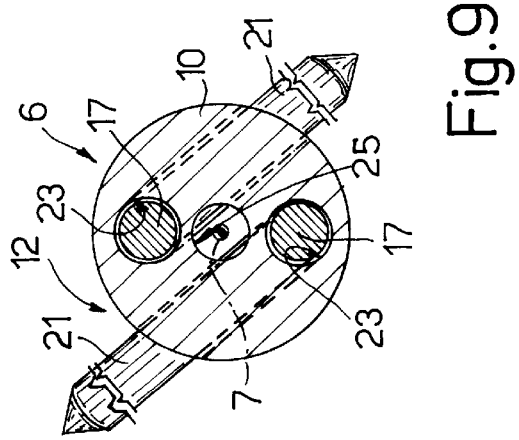

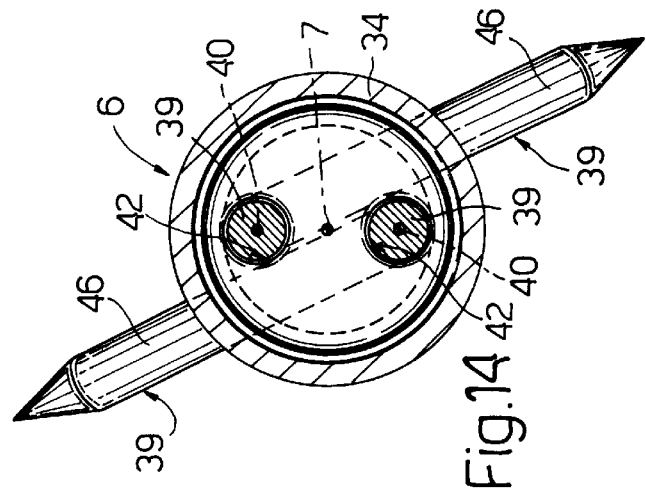
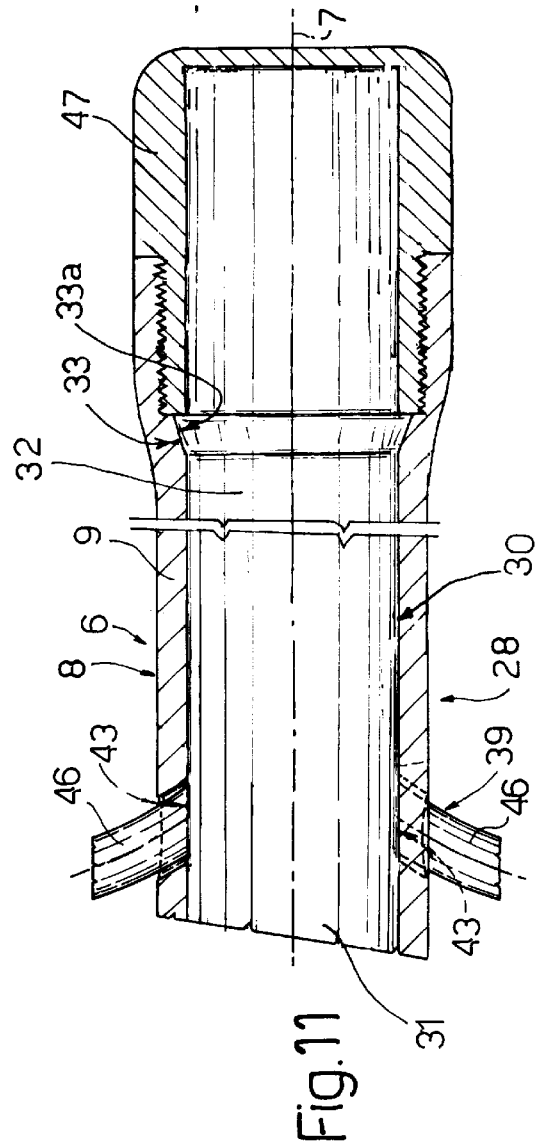
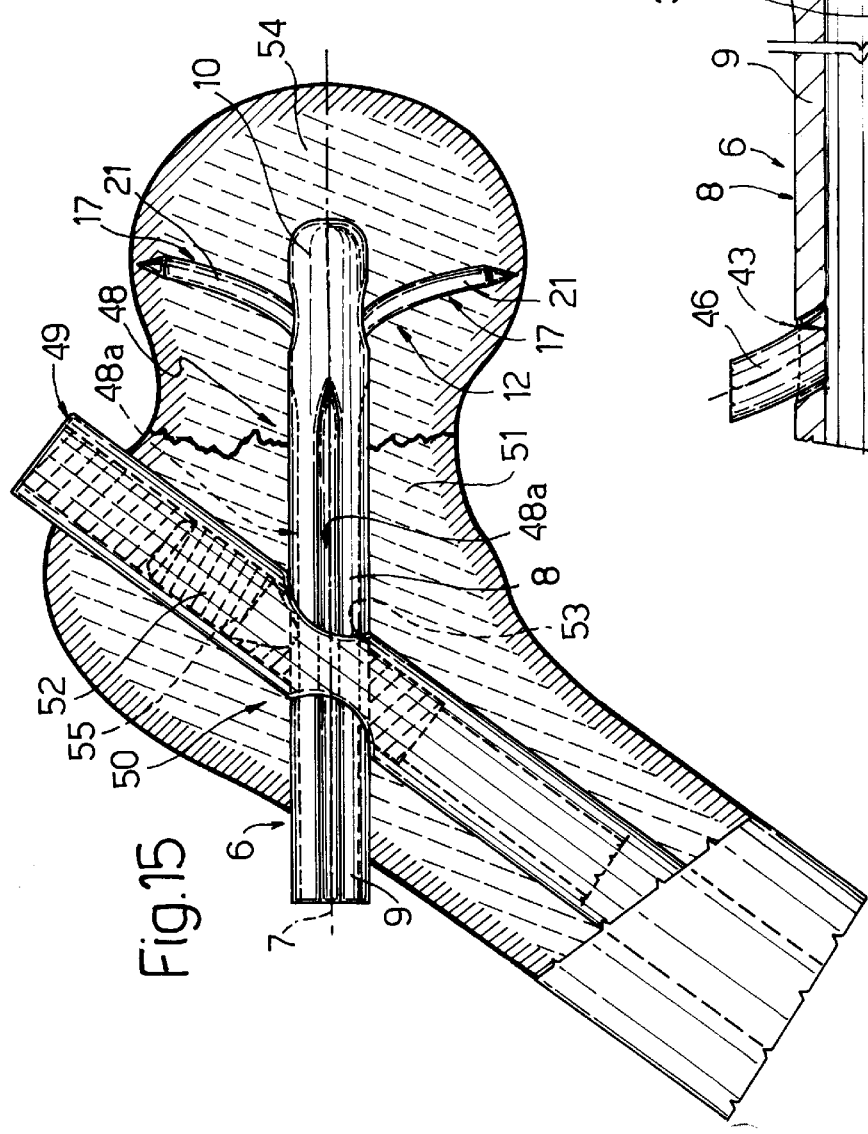

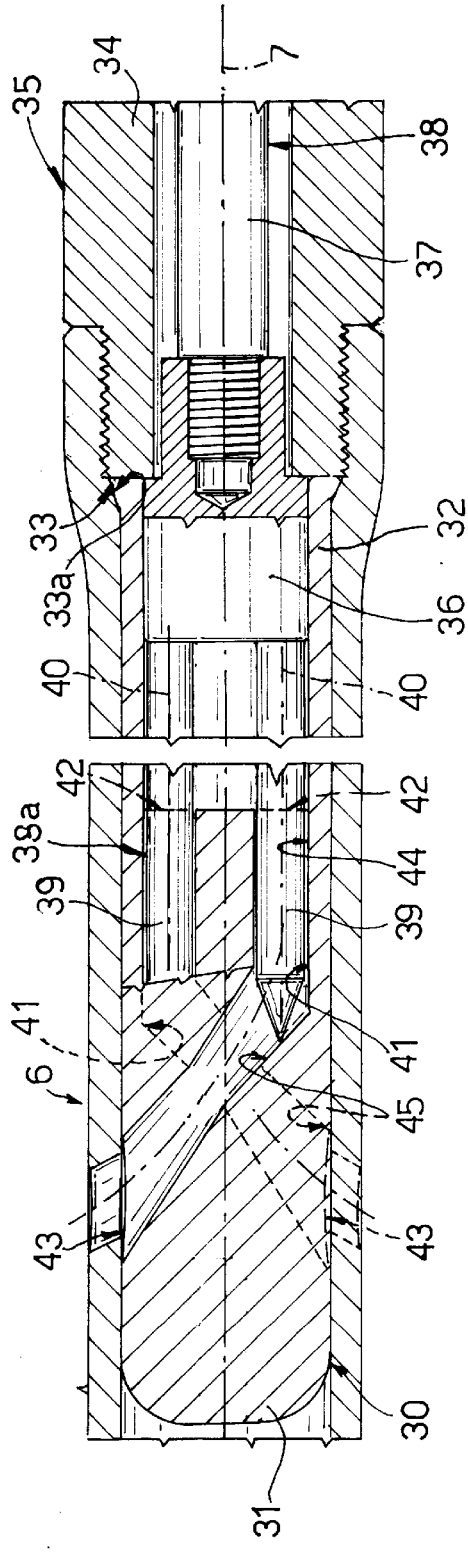
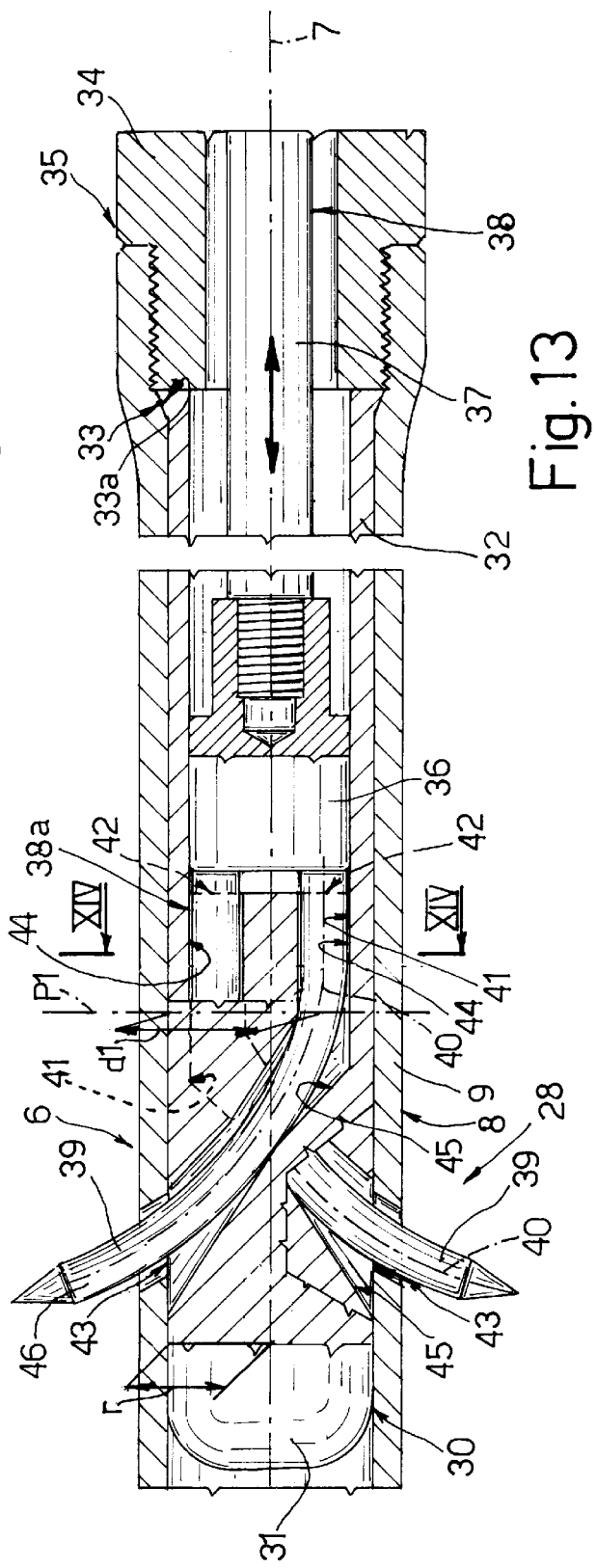

ENDOMEDULLAR DEVICE FOR NAILING
LONG DISTANCE

TECHNICAL FIELD

The present invention relates to an endomedullar device for nailing long bones.

The present invention may be applied to advantage, through not exclusively, to the treatment of long bones such as the femur, to which the following description refers purely by way of example.

BACKGROUND ART

For femur treatment in general, and femur fractures in particular, nailing devices are used which comprise a cannulate metal rod for insertion inside the medullar canal of the femur; and connecting the terminal portions of the cannulate rod to the corresponding terminal portions of the bone.

To connect portions of the rod to the corresponding portions of the bone, through screws are normally used, each extending inside coaxial holes formed in the bone and through the rod.

Though widely used, by virtue of enabling troublefree removal of the cannulate rod from the medullar canal at the end of treatment, through screws involve relatively prolonged surgery, due to the difficulty encountered in most applications in drilling the bone to match the holes in the rod. This is mainly due to the fact that, when inserting the rod, it tends to deform to adapt to the geometry of the medullar canal, thus offsetting the original references of the holes formed in the rod.

In certain Brooker-Wills models, the problem is solved using nailing devices which, in addition to the cannulate rod, also comprise an anchoring assembly in turn comprising two or more tabs. These are hinged to the rod and connected to an activating element so as to rotate, in relation to and about an axis crosswise to the rod, between a withdrawn closed or idle position, wherein the tabs are housed inside the rod, and an extracted or operating position wherein the tabs project through respective openings into the medullar canal and interact, in use, with the bone to make the rod integral with it.

Though successful in solving the above problem, known devices of the aforementioned type present drawbacks of their own, and which are manifested when removing the rod from the medullar canal. To remove the rod, in fact, the tabs must be restored to the withdrawn idle position, which operation is made relatively difficult on account of the fact that, firstly, the tabs are invariably deformed by being forced into the bone and are therefore difficult to withdraw through the respective openings; and secondly, while in the extracted position, a bone deposit forms about the tabs preventing them from being rotated, and from which the tabs can only be freed working from the outside through special openings formed in the bone.

DISCLOSURE OF INVENTION

It is an object of the present invention to provide a device for nailing long bones, and which provides for overcoming the aforementioned drawbacks simply and economically, while at the same time providing for a high degree of reliability.

According to the present invention, there is provided an endomedullar device for nailing long bones; the device comprising an elongated tubular body for insertion inside the bone and presenting an axis; and connecting means for connecting said elongated tubular body to the bone; said connecting means comprising at least first connecting means comprising at least first connecting means associated with one end of the tubular body; characterized in that said first connecting means comprise at least one pair of first deformable nails; first guide means for guiding each of said first nails along a respective path; and first operating means for moving said first nails between a withdrawn idle position wherein the first nails extend at least partly inside said tubular body, and a forward operating position wherein said first nails project outward of said tubular body and are inserted at least partly inside the bone; said first guide means defining, for each first nail, a respective first guide conduit extending along the respecting said path.

BRIEF DESCRIPTION OF THE DRAWINGS

A number of non-limiting embodiments of the present invention will be described by way of example with reference to the accompanying drawings, in which:

FIG. 1 shows a first preferred embodiment of the device according to the present invention and applied to a fractured femur;

FIG. 2 shows a larger-scale view of an end portion of the FIG. 1 device;

FIGS. 3 and 4 show larger-scale, partially sectioned views, with parts removed for clarity, of the FIG. 1 device in two different operating positions;

FIG. 5 shows a partial section along line V—V in FIG. 3;

FIG. 6 shows a larger-scale section of an end portion of the FIG. 3 device;

FIG. 7 shows a section along line VII—VII in FIG. 6;

FIG. 8 shows a larger-scale section, with parts removed for clarity, of an end portion of the FIG. 4 device;

FIG. 9 shows a section along line IX—IX in FIG. 8;

FIG. 10 shows a second preferred embodiment of the device according to the present invention and applied to a fractured bone;

FIG. 11 shows a larger-scale section of an end portion of the FIG. 10 device;

FIGS. 12 and 13 show larger-scale sections of an end portion of the FIG. 10 device in two different operating positions, and part of a device for applying the FIG. 10 device to the fractured bone connected to the end portion;

FIG. 14 shows a section along line XIV—XIV in FIG. 13;

FIG. 15 shows a variation of the FIG. 1 device in association with an endomedullar nail for defining an endomedullar assembly for treating the end portion of a fractured bone.

BEST MODE FOR CARRYING OUT THE INVENTION

Number 1 in FIG. 1 indicates an endomedullar device for nailing a fractured or potentially fracturable long bone.

In the example shown, device 1 is used for treating a femur 2 presenting a break focus 3 between the proximal portion 4 and the distal portion 5 of the bone.

Device 1 comprises a rod 6 which is preferably made of metal, is inserted in use inside the medullar canal of femur 2, presents an axis 7, and in turn comprises a substantially cylindrical tubular body 8 with an end portion 9 extending entirely through proximal portion 4, and a solid end body 10 integral with one end of body 8 and which, in use, extends partly inside distal portion 5.

Device 1 also comprises two connecting or anchoring assemblies 11 and 12 which, in use, provide for positively and releasable connecting rod 6 to portions 4 and 5 of femur 2.

In the example shown, assembly 11 comprises a known screw 13 extending crosswise to axis 7 through a hole formed in portion 9, and partially inside a dead hole formed in proximal portion 4. In an alternative variation (not shown), rod 6 is connected to proximal portion 4 by one or more through screws (not shown) extending substantially perpendicular to axis 7 or, preferably, substantially perpendicular to screw 13.

As shown in FIGS. 3 to 9, anchoring assembly 12 is a cross-nailing assembly, and comprises body 10 in which are formed two conduits 14 presenting respective inlets 15 (FIGS. 3 and 4) communicating with the inside of body 8, and respective outlets 16 communicating externally and formed on diametrically opposite sides of body 8, and respective outlets 16 communicating externally and formed diametrically opposite sides of body 8 and axis 7. Conduits 14 each define a guide for a respective deformable nail 17 presenting a circular section and an externally tapering conical end portion. Nails 17 are defined by the arms of U-shaped rod 17a comprising an intermediate portion 17b (FIGS. 3, 4, 5) locked inside a seat on a tubular slide 18 which is housed inside body 8 and is slid along axis 7 inside body 8 by a known linear actuator 19 (shown only partly).

More specifically, actuator 19 comprises an output rod 19a connected to slide 18 by a threaded coupling 19b, and which, in use, engages body 8 in axially sliding manner to move slide 18 both ways along axis 7 and nails 17 along respective paths 20 (FIGS. 6 and 8). Rod 19a is so controlled as to move slide 18 and nails 17 between a withdrawn idle position wherein slide 18 is adjacent to portion 9, and nails 17 extend parallel to axis 7 inside and adjacent to the inner surface of body 8, and partially engage conduits 14, and a forward operating position wherein slide 18 is moved towards body 10, and nails 17 cross each other, and present respective end portions 21 projecting outward of body 8 through respective outlets 16 and extending, in use, through distal portion 5 (FIG. 1).

With reference to FIGS. 6 and 8, each conduit 14 comprises an inlet portion 23 communicating with the inside of body 8; and an outlet portion 24 communicating with respective portion 23 at one end, and externally at the other end. More specifically, portions 23 are straight, present a diameter approximately equal to but no smaller than the diameter of nails 17, and extend parallel to and eccentrically in relation to axis 7 on diametrically opposite sides of a through hole 25 coaxial with axis 7 and enabling the passage, in use, of a known guide wire (not shown) for inserting rod 6 inside femur 2.

Portions 24 also extend on diametrically opposite sides of hole 25, but crosswise to axis 7 and in respective directions crosswise to each other, and are slightly curved or at any rate such as to gradually bend respective nails 17 by substantially 90° so that end portions 21 of nails 17 project from respective outlets 16 and extend in respective directions substantially perpendicular to axis 7 (FIGS. 8 and 9). More specifically (FIGS. 6 and 8), each portion 24 presents a length, the projection "d" of which on to a plane P perpendicular to axis 7 is much greater than the outer radius "r" of body 8.

Operation of device 1 will now be described—as applied by way of example to the treatment of femoral fractures—as of the condition in which screw 13 is disconnected from rod 6, and nails 17 are set to the withdrawn idle position wherein portions 21 fully engage portions 23 of respective conduits 14.

As of the above condition, the guide wire (not shown) is first inserted in known manner inside femur 2; rod 6 is connected to the guide wire (not shown) which engages in sliding manner hole 25 and extends through body 8; and rod 6 is inserted in known manner inside the medullar canal of femur 2 so that body 10 partially engages distal portion 5.

At this point, the guide wire (not shown) is withdrawn from femur 2; and slide 18 is connected to rod 19a of actuator 19 and pushed gradually towards body 10 to feed nails 17 gradually along respective paths 20.

As they move forward, nails 17 travel along portions 24 inside which the are gradually bent in such a manner as to extend crosswise to body 10 and each other, and to extend crosswise to body 10 and each other, and to eventually come out of respective outlets 16 in opposite directions and engage femur 2 from the inside.

Rod 19a of actuator 19 then is disconnected from slide 18 and withdrawn from body 8; and end portion 9 of rod 6 is connected integral with proximal portion 4 of femur 2 by inserting screw 13 inside portion 4 and through rod 6 in known manner.

After a sufficient period of time to allow femur 2 to knit, screw 13 is withdrawn from proximal portion 4; rod 19a of actuator 19 is again inserted inside body 8 and connected to slide 18; and, by means of actuator 19, slide 18 and nails 17 are eased back into their respective idle positions. More specifically, as slide 18 is withdrawn, end portions 21 of nails 17 gradually release femur 2 and travel backwards along respective conduits 14 inside which nails 17 are again deformed and restored substantially to the initial condition.

Upon slide 18 moving into the withdrawn idle position, rod 19a of actuator 19 is disconnected from slide 18 and withdrawn form rod 8; and rod 6, now in no way connected to femur 2, is simply pulled out.

The embodiment shown in FIGS. 10 to 14 relates to an endomedullar device 27 similar to device 1, and the component parts of which are indicated wherever possible using the same numbering system.

Rod 6 of device 27 is connected to proximal portion 4 of femur 2 by means of an anchoring assembly 28 similar to assembly 12 and comprising an elongated cylindrical plugging body 30 (FIGS. 11, 12, 13) which, in use, is housed inside portion 9 and presents an outside diameter approximately equal to but no larger than the inside diameter of portion 9. Portion 9 presents an internal thread which, in use, is engaged by the threaded end portion of a sleeve 34 (FIGS. 12, 13) extending coaxially with axis 7 and which, in use, provides for locking body 30 in relation to portion 9, and forms part of a device 35 for applying device 27 to femur 2.

Tubular portion 32 of body 30 house in axially sliding manner a slide 36 similar to slide 18 and connectable, by means of a threaded coupling, to the output rod 37 of a linear actuator 38 for moving slide 36 in both directions along axis 7.

Slide 36 is fitted with a U-shaped rod 38a, the arms of which define respective nails 39 geometrically similar to nails 17 and which, in the same way as nails 17, provide for cross-nailing portion 9 to proximal portion 4 of femur 2.

More specifically, nails 39 are moved by slide 36 along respective paths 40 similar to paths 20 as regards both shape and location in relation to rod 6, and are guided along paths 40 by respective conduits 41 similar to conduits 14 and formed in portion 31 of body 30.

More specifically (FIGS. 12 and 13), conduits 41 present respective inlets 42 communicating with the inside of portion 32, and respective outlets 43 communicating external through respective holes formed in and on diametrically opposite sides of portion 9. Like conduits 14, each conduit 14 comprises an inlet portion 44 communicating with the inside of portion 32; and an outlet portion 45 communicating at one end with respective inlet portion 44, and externally at the other end. More specifically, portions 44 are straight, present a diameter approximately equal to but no smaller than the diameter of nails 39, and extend parallel to and eccentrically in relation to axis 7.

Portions 45 extend crosswise to axis 7 in respective directions crosswise to each other and coincident with respective paths 40, and are curved with their concavity facing the same side as portion 32, so as to gradually bend respective nails 39 by substantially 90° so that the end portions 46 of nails 39 come out of respective outlets 43 and extend in directions substantially perpendicular to axis 7 (FIG. 13). More specifically (FIG. 13), each portion 45 presents a length, the projection "d1" of which on to a plane P1 perpendicular to axis 7 is much greater than the outside radius "r" of body 8.

In actual use, rod 6 is connected to femur 2 by means of assembly 12; rod 19a of actuator 19 is withdrawn from body 8; body 30; with nails 39 partially engaging conduits 41, and with slide 36 housed inside portion 32, is inserted inside body 8 so that shoulders 33 and 33a contact each other; and sleeve 34 is screwed on to portion 9 to lock body 30 in relation to body 8.

At this point, slide 36 is connected to rod 37 of actuator 38 and is moved by actuator 38 along axis 7 towards portion 31 of body 30; during which movement, nails 39 are fed along respective paths 40 and into the operating position engaging femur 2 in the same way as for assembly 12.

After driving end portions 46 of nails 39 into proximal portion 4, rod 37 of actuator 38 is disconnected from rod 6; and a cap 47 is screwed on to rod 6 as shown in FIG. 11.

The FIG. 15 variation relates to an endomedullar device 48 similar to device 1 and the component parts of which are indicated wherever possible using the same numbering system.

Device 48 differs from device 1 by presenting no portion 9 of rod 6, and by the outer surface of body 8 presenting a number of outer axial grooves 48a. In use, rod 6 of device 48 is fitted to femur 2 by means of assembly 12, and cooperates with a known pin 49 with which it defines a nailing assembly 50 for treating fractures of the neck 51 of femur 2.

As shown in FIG. 15, pin 49 is inserted inside the medullar canal of femur 2, and presents an end portion 52 in turn presenting a transverse through hole 53 engaged in sliding manner by body 8 of rod 6. Rod 6 extends crosswise to portion 52 of pin 49 and, in use, inside neck 51 and head 54 of femur 2, and is connected to head 54 by assembly 12 and adjustably to pin 49 by means of a threaded pin 55 which engages a threaded portion of which engages a respective groove 48a.

In addition to being extremely reliable functionally, devices 1, 27 and 48 therefore provide, as compared with known devices for greatly reducing operating time and, in particular, for locking rod 6 firmly to femur 2, and enabling trouble free removal of rod 6 from the medullar canal at the end of the treatment.

This is mainly due to the fact that, in each of the devices described, rod 6 is locked both angularly and axially inside the medullar canal by a respective pair of nails 17, 39, which are pushed by respective slides 18, 36 along respective conduits 14, 41, and engage femur 2 from the inside by coming out of rod 6 in opposite directions substantially perpendicular to axis 7 and without being bent sharply, in particular at right angles.

As regards withdrawal of rod 6 from the medullar canal, this is simplified enormously by the ease with which the connection between rod 6 and femur 2 effected by nails 17, 39 is eliminated at all times, and particularly in the presence of bone deposits about the nails or at outlets 16, 43, by simply withdrawing nails 17, 39 which, by virtue of presenting a circular section, of presenting no right angle bends, and above all of also being guided during withdrawal by respective conduits 14, 41, may be withdrawn by operating externally on respective slides 18, 36 in much the same way as for insertion.

As regards nailing assembly 12, this obviously provides for firmly connecting rod 6 to the distal portion 5 of femur 2 by operating externally, and more specifically from the proximal portion 4 of femur 2.

Finally, the particular design characteristics of devices 1, 27 and 48 provide for both connecting them to the fractured femur 2 and disconnecting them from the knitted femur 2 with substantially no need for X ray equipment, the long-term use of which, as is known, is extremely harmful to the health of the surgeon.

Clearly, changes may be made to devices 1, 27 and 48 as described and illustrated herein without, however, departing from the scope of the present invention. In particular, nails 17, 39 and rod 6 may present a different section from that described; and nails 17, 39 may differ in number and be connected differently to the slide.

Finally, in addition to the femur, devices 1 and 27 may also be used for treating long bones in general, e.g., the tibia, and in particular for treating slightly curved long bones for which a curved rod 6 is essential. In these cases also, rod 6 may be connected to the fractured bone by virtue of nails 17, 39 being flexible and therefore insertable inside tubular body 8 along slightly curved paths.

We claim:

1. An endomedullar device for nailing long bones; the device comprising an elongated tubular body for insertion inside the bone and presenting an axis; and connecting means for connecting said elongated tubular body to the bone; said connecting means comprising at least first connecting means associated with one end of the tubular body; wherein said first connecting means comprising at least one pair of first deformable nails; first guide means for guiding each of said first nails along a respective path; and first operating means for moving and deforming said first nails between a withdrawn idle position wherein the first nails extend at least partly inside said tubular body and a forward operating position wherein said first nails project outside of said tubular body and are inserted at least partly inside the bone; said first guide means defining, for each first nail, a respective first guide conduit extending along the respective said path and wherein each said first guide conduit comprises a first portion extending crosswise to said axis and presenting a length, the projection of which on to a plane perpendicular to said axis is greater than half the transverse dimension of the elongated tubular body measured in said plane.

2. A device as claimed in claim 1, wherein each said first portion is curved.

3. A device of any one of claims 1 or 2, wherein each said a first guide conduit includes a substantially straight portion.

4. A device as claimed in claim 3, wherein said second portions extend parallel to said axis and communicate with the inside of said tubular body.

5. A device as claimed in claim 4, wherein said second portions extend eccentrically in relation to said axis.

6. A device of claim 3 wherein said first conduits present respective outlets; and said first nails project from respective said outlets in directions substantially perpendicular to said axis.

7. A device of claim 3 wherein said first nails present a substantially circular cross section and an outwardly tapering free end portion.

8. A device of claim 3 wherein said first guide means comprise an end body connected integral with one end of said elongated tubular body; said first conduits being formed in said end body.

9. A device of claim 3 wherein said first operating means comprise a slide slidable inside said tubular body.

10. A device of claim 3 wherein said connecting means also comprise second connecting means separate from and substantially similar to said first connecting means.

11. A device as claimed in any one of claims 1 or 2 wherein said first conduits present respective outlets; and said first nails project from respective said outlets in directions substantially perpendicular to said axis.

12. A device as claimed in claim 11, wherein said outlets are formed substantially on opposite sides of said axis.

13. A device of any one of claims 1 or 2 characterized in that said first nails present a substantially circular cross section and an outwardly tapering free end portion.

14. A device of any one of claims 1 or 2 characterized in that said first guide means comprise an end body connected integral with one end of said elongated tubular body; said first conduits being formed in said end body.

15. A device as claimed in claim 14, wherein said end body is formed in one piece with said elongated tubular body, and presents a through hole coaxial with said axis.

16. A device of any one of the foregoing claims 1 or 2 wherein first operating means comprise a slide slidable inside said tubular body.

17. A device of any one of claims 1 or 2 wherein said connecting means also comprise second connecting means separate from and substantially similar to said first connecting means.

* * * * *